United States Patent [19]

Schneider

[11] Patent Number: 4,857,042
[45] Date of Patent: Aug. 15, 1989

[54] BODY FLUID COLLECTION DEVICE

[75] Inventor: James G. Schneider, St. Louis, Mo.

[73] Assignee: Sherwood Medical Company, St. Louis, Mo.

[21] Appl. No.: 168,834

[22] Filed: Mar. 16, 1988

[51] Int. Cl.$^4$ ............................................. A61M 1/03
[52] U.S. Cl. ...................................... 604/4; 128/767;
128/DIG. 1.2; 222/105; 383/35; 383/109;
604/131; 604/317; 604/406
[58] Field of Search ....................... 604/4–6,
604/131–133, 317, 319, 322, 403, 406, 408, 410,
415, 318, 320, 321; 128/760, 767, 768, DIG. 12;
383/35, 109, 119, 127, 43; 222/105, 107, 215

[56] References Cited

U.S. PATENT DOCUMENTS

| | | | |
|---|---|---|---|
| 3,473,532 | 10/1969 | Eisenberg | 128/227 |
| 3,557,786 | 1/1971 | Barr, Sr. et al. | 128/214 |
| 3,648,698 | 3/1972 | Doherty | 604/319 |
| 3,724,461 | 4/1973 | Eisenberg | 604/408 |
| 3,734,154 | 5/1973 | Polk | 150/9 |
| 4,006,745 | 2/1977 | Sorenson et al. | 128/214 R |
| 4,105,031 | 8/1978 | Kurtz et al. | 128/276 |
| 4,161,179 | 7/1979 | Abramson | 128/278 |
| 4,317,478 | 3/1982 | Babbidge | 383/35 |
| 4,429,693 | 2/1984 | Blake et al. | 604/73 |
| 4,443,220 | 4/1984 | Hauer et al. | 604/408 |
| 4,540,413 | 9/1985 | Russo | 604/320 |
| 4,583,972 | 4/1986 | Hunter, III et al. | 604/133 |
| 4,645,486 | 2/1987 | Beal et al. | 604/4 |
| 4,781,707 | 11/1988 | Boehringer et al. | 604/319 |
| 4,798,578 | 1/1989 | Ranford | 604/4 |

FOREIGN PATENT DOCUMENTS

| | | | |
|---|---|---|---|
| 2330101 | 1/1975 | Fed. Rep. of Germany . | |
| 3244151 | 5/1984 | Fed. Rep. of Germany | 604/317 |
| 1049763 | 12/1953 | France . | |

OTHER PUBLICATIONS

Deknatel, "Why transfuse if you can reinfuse with the Pleur-Evac$^R$ Autotransfusion System?", The Journal of Thoracic and Cardiovascular Surgery, vol. 93, No. 2, Feb. 1987.

Primary Examiner—C. Fred Rosenbaum
Assistant Examiner—Mario Costantino
Attorney, Agent, or Firm—Stanley N. Garber; Andrew J. Beck; Richard D. Allison

[57] ABSTRACT

An autotransfusion device usable with a chest drainage unit includes a collapsible fluid collection bag assembly having pliable fluid collection bag, a pair of stiffener members adjacent the opposed sides of the bag, and an enclosure sealingly connected to the bag securing the stiffeners in place. A fluid inlet, gas outlet, and a blood outlet are connected to the bag. A holder is dimensioned to compress the opposed edges of the bag assembly to cause the stiffeners to bow outwardly in opposite directions and expand the collection bag.

23 Claims, 4 Drawing Sheets

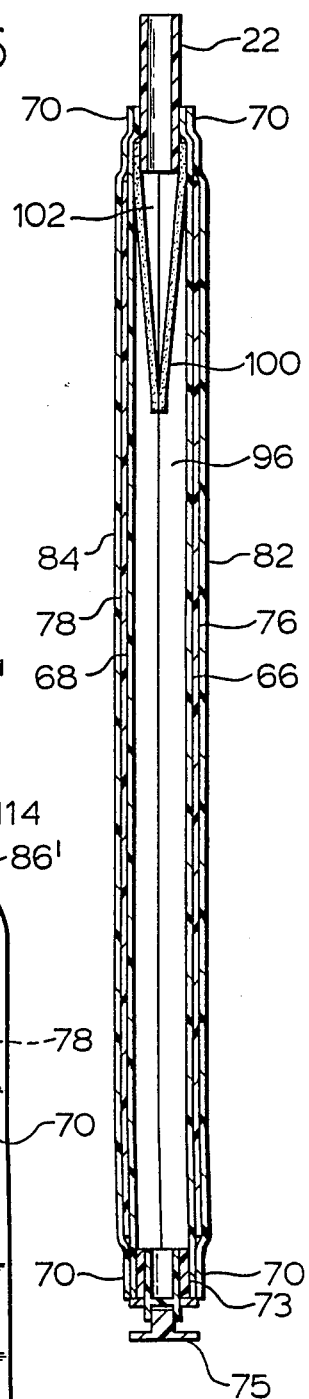
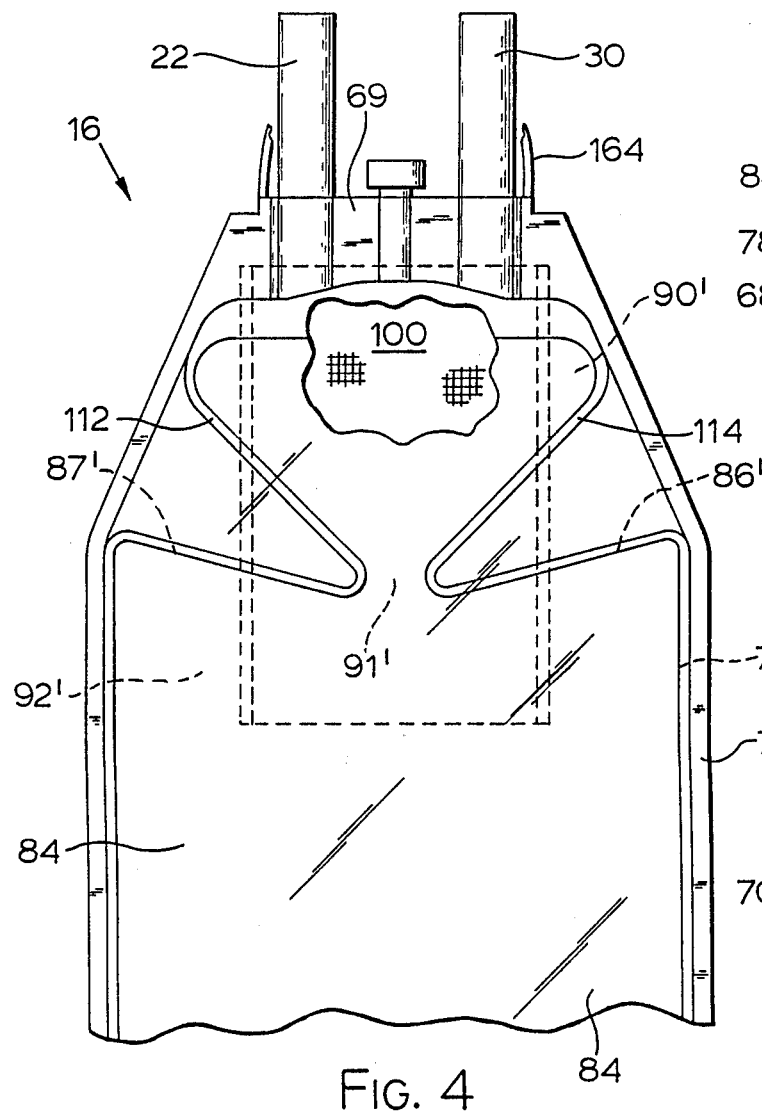
FIG. 5
FIG. 4

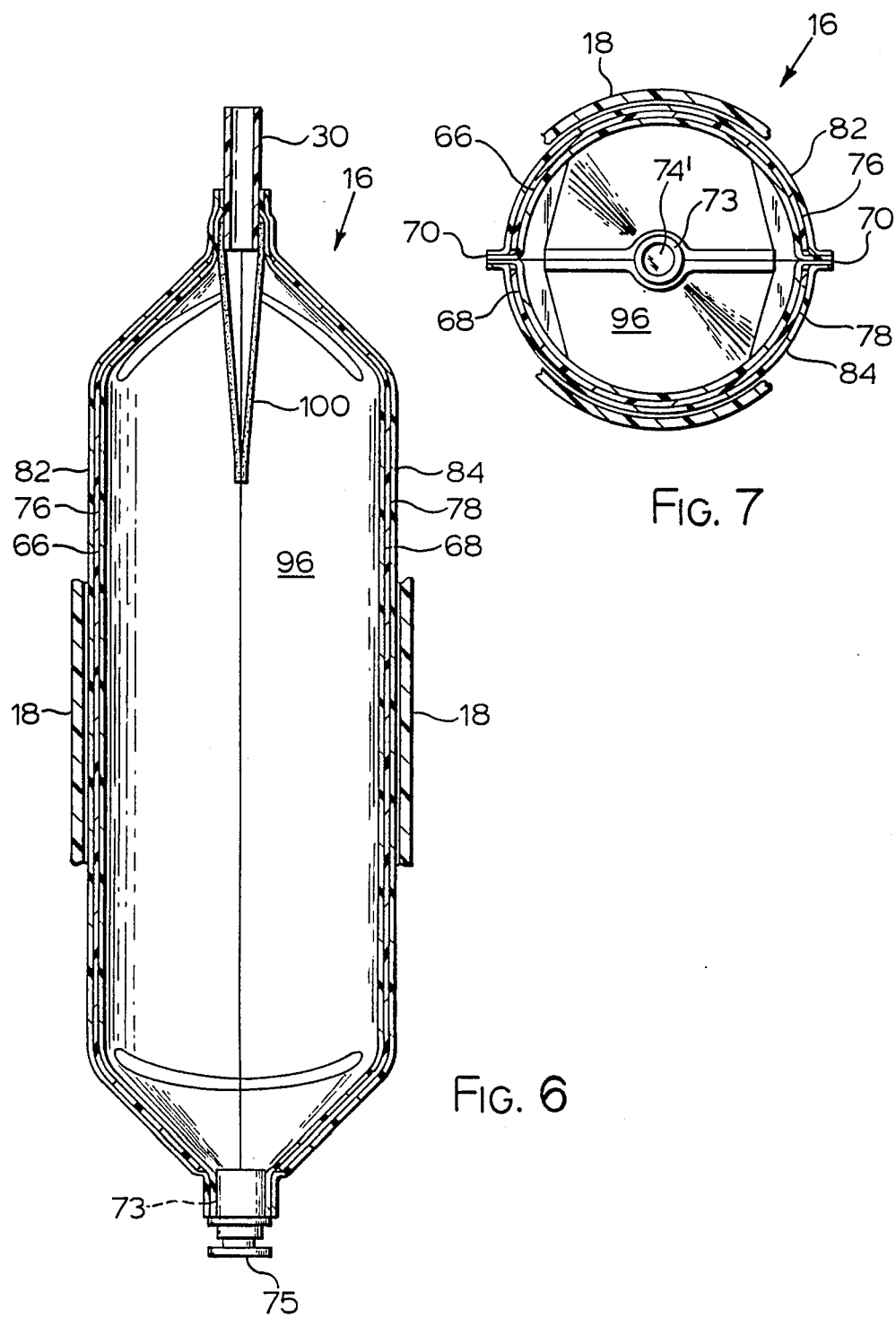

BODY FLUID COLLECTION DEVICE

TECHNICAL FIELD

This invention relates to body fluid collection devices and more particularly to a collapsible body fluid collection autotransfusion device.

BACKGROUND

More recently, auxiliary autotransfusion blood collection containers have been employed with chest drainage units which employ suction during fluid collection and which permit reinfusion of the collected blood to the patient thereby avoiding the necessity of infusing stored blood from another person and the possibility of transmitting a disease to the patient.

Some autotransfusion devices of this type have had certain problems or disadvantages associated with them. A blood collection container or bottle which is non-collapsible has been connected to a chest drainage unit such that suction is applied through the container to the mediastinal or plueral cavity of a patient with the container receiving drainage blood. In order to reinfuse the blood into the patient from the non-collapsible container however, the bottle must be vented to atmosphere to allow the collected blood to flow from such container to the patient. In such a case, air is in contact with the blood and may affect its characteristics. Also, an air filter must be used to filter air from the atmosphere into the container during infusion.

Collapsible blood collection containers such a collapsible bags have been used in order to avoid the necessity and problems of venting the container during reinfusion. However, such collapsible bag containers have also had certain problems and disadvantages. For example, the collapsible bag requires apparatus to maintain the bag in an expanded condition during blood collection in spite of the negative pressures or suction forces within the bag. In general, this has caused the bag and the bag expanding device to be relatively complicated and expensive. In some cases, the bags, when expanded, took on indefinite shapes which produced indefinite volumes and thus provided inaccurate or unreliable indications of the amount of blood collected at any time.

OBJECTS AND SUMMARY OF THE INVENTION

It is therefore an object of the present invention to provide an improved autotransfusion blood collection device which is expandable for collecting blood with suction applied thereto, while maintaining a predetermined expanded condition, which is collapsible for reinfusion purposes, and which substantially avoids the above-mentioned problems and disadvantages associated with prior collapsible bag autotransfusion devices.

Another object is to provide an improved collapsible fluid collection container assembly having a pliable collection bag and flexible stiffeners external to the bag for expanding the collection bag and wherein bonding between the materials of the bag and the stiffeners is not necessary.

Still another object is to provide improved autotransfusion apparatus and method of making it which is connectable with a chest drainage unit and which includes a pliable collection bag assembly expandable for the collection of blood and other body fluid from a patient, and collapsible for infusing collected blood back into the patient, and wherein the chance of blood leakage from the apparatus is minimized.

In accordance with one aspect of the present invention, a collapsible body fluid collection assembly is provided which includes a collapsible fluid collection bag, a pair of flexible stiffening members disposed respectively adjacent the opposed exterior sides of the bag, and an enclosure enclosing the stiffener members between the bag enclosure.

In accordance with another aspect of the present invention, and autotransfusion device is provided which includes a body fluid collection bag assembly having a collapsible bag, stiffeners outside the bag and adjacent the opposed sides of the bag, and an enclosure sealingly enclosing the stiffener between the bag and the enclosure, and a holder for receiving the bag and the stiffener members to apply compressive forces on the side edges of the assembly to maintain the bag in an expanded condition for receiving blood.

These as well as other objects and advantages of the present invention will become apparent from the following detailed description and accompanying drawings.

BRIEF DESCRIPTION OF THE DRAWINGS

FIG. 4 is an enlarged partial side view of the upper portion of the bag assembly of FIG. 3 with parts broken away and rotated 180° about the vertical axis;

FIG. 5 is a cross-sectional view taken along the line 5—5 of FIG. 3;

FIG. 6 is a cross-sectional view taken along the line 6—6 of FIG. 1; and

FIG. 7 is a cross-sectional view taken along the line 7—7 of FIG. 1.

DESCRIPTION OF THE PREFERRED EMBODIMENT

Figure 1:
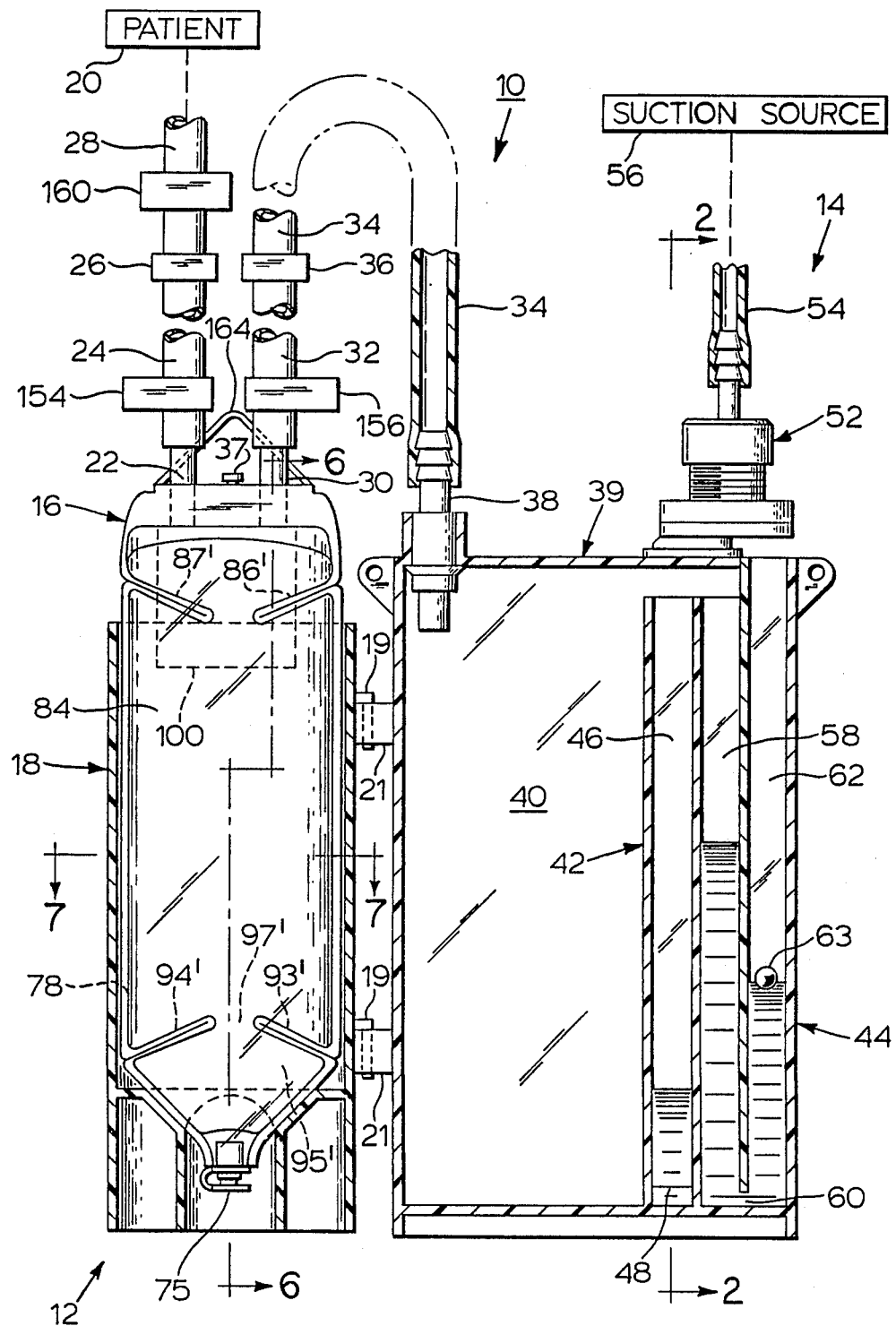
FIG. 1 is an elevational view, partly in section, of a chest drainage system including an autotransfusion device in accordance with a preferred embodiment of the present invention.

Referring now to the drawings and particularly FIG. 1, a chest drainage system 10 is shown including an autotransfusion blood collection device 12 according to the present invention connected to the side of a chest drainage unit 14. The device 12 includes an autotransfusion or blood collection or reinfusion bag assembly 16 and a bag expanding member or holder 18 receiving the bag assembly 16 and connected by any suitable means to the side of the chest drainage unit 14, for example, by a pair of supporting hooks 19 respectively received in eyelets 21 connected to unit 14. As will be discussed hereafter, the holder 18 maintains the collapsible bag assembly 16 in an expanded condition for receiving body fluids including blood from the mediastinal or plueral cavity of a patient indicated at 20.

The collapsible blood collection and reinfusion bag assembly 16 has an inlet 22 communicating with the interior of the bag assembly and shown connected to a tube 24. Tube 24 is connected through a tube connector 26 to the proximal end of a patient tube 28 which is connected through a catheter to the plueral cavity of patient 20. Spaced from the inlet 22 at the top of the bag assembly 16 is a gas outlet 30 communicating with the interior of the bag assembly and thereby inlet 22. Gas outlet 30 is connected to a tube 32 which, in turn, is connected to a tube 34 through a tube connector 36. Tube 34 is connected to an inlet 38 of the chest drainage unit 14. An auxiliary inlet 37 between the inlet and outlets 22 and 30 communicates with the interior of the bag and is preferably a conventional self-sealing port which can be penetrated by a syringe needle for introducing a substance to the bag assembly 16, for example, an anticoagulant.

Figures 2, 3:
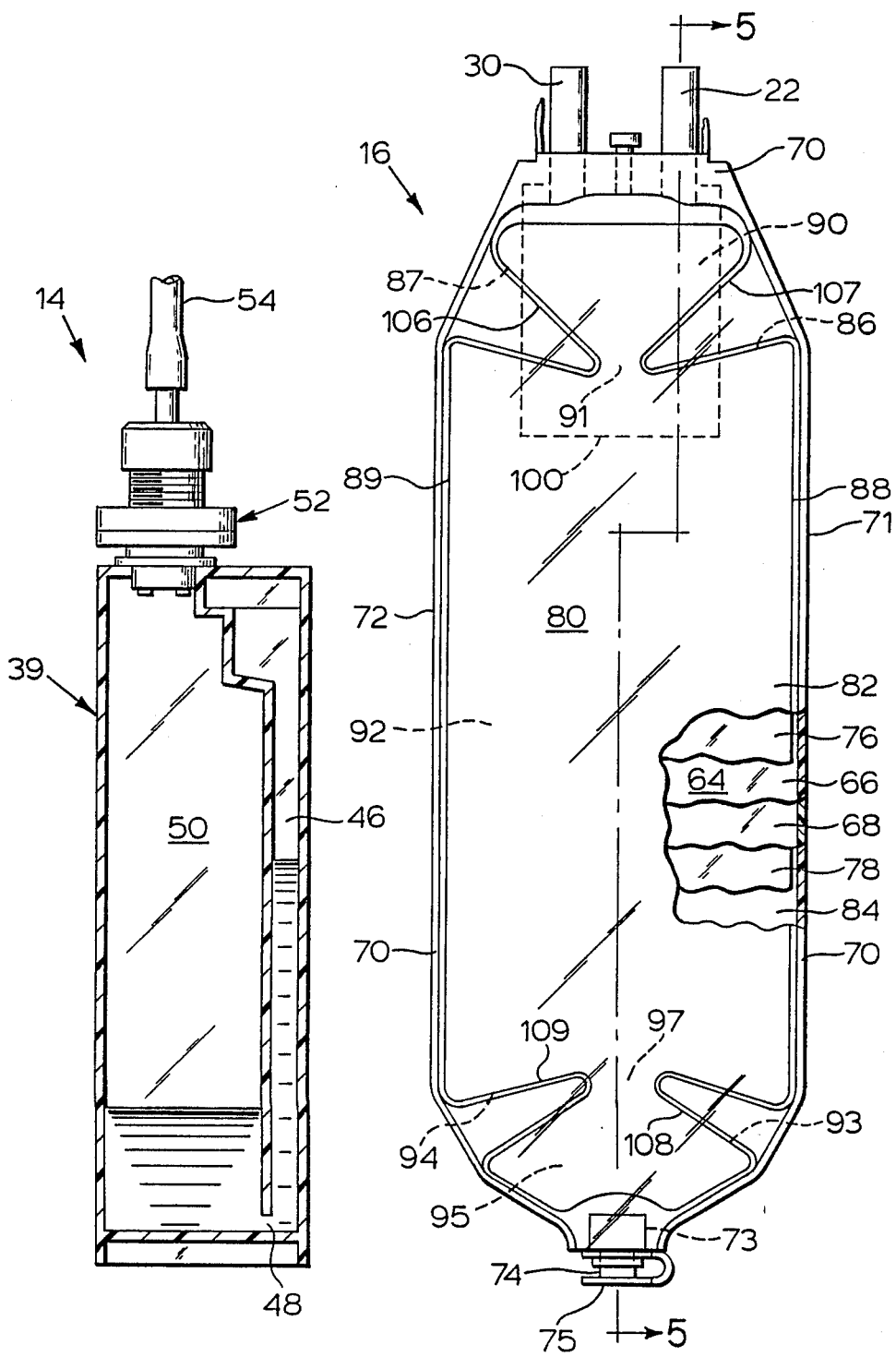
FIG. 2 is a cross-sectional view taken along the line 2—2 of FIG. 1.
FIG. 3 is an enlarged side view of the bag assembly of FIG. 1 rotated 180° about the vertical axis in a collapsed condition and as manufactured.

Chest drainage unit 14 is shown for illustration including a housing 39, preferably of rigid transparent plastic, for example, a polycarbonate or the like. The housing 39 includes a fluid collection chamber 40, an underwater seal chamber indicated generally at 42, and a liquid manometer indicated at 44. The liquid underwater seal includes a relatively narrow vertical channel 46 open at the top where it is in fluid communication with a collection chamber 40. Channel 46 has an opening 48 at the bottom which communicates with a relatively large chamber 50 of the water seal 42 as seen in FIG. 2. Connected to the top of outlet chamber 50 is a suction regulator 52 that is connected by a flexible tube 54 to a source of suction 56 (FIG. 1) which source may be a conventional hospital wall suction source. The liquid manometer includes a vertical channel 58 connected in fluid communication with collection chamber 40 at the top and by a passage 60 at the bottom to a vertical column 62 that is open at the top to the atmosphere. Both the underwater seal 42 and the liquid manometer 44 are shown provided with suitable quantities of a liquid such as water.

When the chest drainage system 10 is operating, a partial vacuum or negative pressure exists in the underwater seal chamber 50 (FIG. 2), and any air or gas from the patient flows from tube 28 (FIG. 1) into the upper portion of bag assembly 16 through inlet 22, then, into outlet 30, into collection chamber 40, downwardly through the water in underwater seal channel 46, through the bottom opening 48, upwardly through the water in outlet chamber 50 (FIG. 2) and then to the suction source 56 through regulator 52. The underwater seal 42 prevents any atmospheric air from flowing through the unit to the patient. Because the liquid manometer is responsive to the pressure in collection chamber 40, the level of the liquid and an indicating float 63 in the liquid manometer 44 will vary in height in accordance with negative pressure changes in the collection chamber 40, thus providing an indication of the suction level or negative pressure in the collection chamber 40 and therefore in the mediastinal or plueral cavity of the patient. The regulator 52 is adjustable to regulate or limit the suction or negative pressure in the collection chamber 40 to a desired and safe value. The construction and operation of the chest drainage unit 14 including that of the suction regulator 52 are shown described in detail in U.S. Pat. No. 4,372,336 and are hereby incorporated herein by reference. In the present construction however, blood flows in the collection chamber 40 only after the bag assembly 16 over-fills.

The collapsible blood collection and reinfusion bag assembly 16 is shown in FIGS. 3-5 in a collapsed condition and as manufactured, that is, without any compressive forces being applied to the assembly so that the assembly is in its substantially flat condition prior to being inserted into the holder 18. Assembly 16 includes a collapsible, pliable blood collection and reinfusion bag 64 formed of a pair of opposed, parallel facing sheet members or panels 66 and 68 connected and sealed together about the periphery of the bag such as by a peripheral weld seam 70 and which may be formed by conventional heat sealing such as RF sealing or heat and pressure welding. The peripheral seal 70 extends around a manifold 69 (FIG. 4) at the top of the bag assembly which is integrally connected with the inlet 22 and gas outlet 30 to connect them to the bag 64 in fluid communication with the interior of the bag. The seal 70 extends down the longer side edges of the bag assembly 16, indicated at 71 and 72, and around a tubular blood outlet 73 at the bottom of the assembly which is also in fluid communication with the interior of the bag. The blood outlet 73 is normally closed by a needle piereable plug 74 received in outlet 73 and having an integrally tethered cap 75. The plug 74 is shown in FIG. 7 provided with a conventional integral piercable seal 74'. The panels 66 and 68 of bag assembly 16 are formed of flexible or pliable material, preferably polyurethane or a relatively pliable or soft polyvinyl chloride (PVC) so that the bag is readily and easily collapsible and expandable. Preferably, panels 66 and 68 are transparent as indicated in the drawings and of thermoplastic material so that weld seam 70 can be readily formed. The manifold 69 and outlet 73 may be made of a suitable plastic such as relatively rigid PVC.

Bag assembly 16 includes a pair of flexible bag stiffener members or panels 76 and 78 respectively disposed in parallel facing relation adjacent the outer surfaces of panels 66 and 68 of bag 64 and an enclosure or outer bag 80 sealingly enclosing the collection bag 64 and stiffeners members 76 and 78. Stiffener panels 76 and 78 are in the form of generally flat transparent sheet members of relatively stiff material, preferably, of a relatively rigid flexible plastic sheet material such as of resilient, rigid PVC or polyester terephthalate (PET-G). The enclosure 80 may be formed of the same material as the collection bag 64, and preferably of a thermoplastic material such as polyurethane or it may be of a soft or pliable PVC sheet material in the form of interconnected pliable panels 82 and 84. The enclosure panels 82 and 84 are respectively sealed to the peripheral edges of the collection bag panels 66 and 68 by the peripheral seam 70.

The stiffening members 76 and 78 are identical in shape in the illustrated embodiment, and each is symmetrical about the vertical or longitudinal axis. Stiffener panel 76 is provided at the top with a pair of upper angular slots 86 and 87 which extend inwardly and downwardly respectively from the opposed longer side edges of the panel, indicated at 88 and 89, forming an upper stiffener portion 90 above the slots with a relatively narrow neck portion 91 integrally connecting the upper portion 90 to a relatively large main portion 92. Similarly, panel 78, as seen in FIG. 4, has like slots 86' and 87', upper portion 90', neck portion 91' and main portion 92'. Panel 76 (FIG. 3) also has a pair of bottom angular slots 93 and 94 which pair extends respectively from the side edges 88 and 89 of the panel and upwardly and inwardly. The inner ends of the lower slots are spaced from each other to provide a relatively narrow neck portion 94 that connects a lower portion 95 to the major central portion 92. Likewise, panel 78 (FIG. 1) has like slots 93' and 94, neck portion 94', and a lower portion 95'. The neck portions of the stiffener panels are relatively narrow so that they are relatively flexible and readily bend radially inwardly to allow the upper, main and lower portions of each stiffener panel to bend in a manner to form the expanded bag assembly 16 as seen in FIGS. 1, 6 and 7 when opposed compressive forces are applied to the opposed sides 71 and 72 of the assembly 16 by holder 18, as discussed hereinafter. Such forces, in turn, apply compressive forces to the opposed side edges 88 and 89 of the stiffener panels 76 and 78 so that portions of the stiffener panels between the opposed side edges bow or bend outwardly in opposite directions. Since the stiffener and collection bag panels are secured together by the enclosure 80, the pliable collection bag panels 66 and 68 also bow outwardly to expand the interior of the collection bag 64 providing a body fluid collection chamber indicated at 96 in FIGS. 5–7. The bag assembly 16 thus has an essentially cylindrical central portion, and tapered upper and lower end portions after insertion in the holder 18, as best seen in FIGS. 1, 6 and 7.

Connected within the upper portions of bag 64 is a filter 100, as best seen in FIGS. 4 and 5. The illustrated filter is shown including a fine plastic screen in the form of a filter bag having a filter chamber 102 closed about its periphery and with the inlet 22 and gas outlet 30 sealed to the filter and extending from the exterior of bag assembly 16 into the filter chamber 102.

Filter 100 may be formed by cutting suitable blood filtering sheet mateial, such as a thermoplastic screen, for example, a polyester or nylon screen-like material. The filter material may be cut into a rectangular shape and folded in half to provide a fold at the bottom. The opposed sides may be welded, fused or melt bonded together and with the opposed ends of the filter at the top weld sealed about the inlet 22, outlet 30, and auxiliary inlet 37 of the manifold by the peripheral weld or seal 70.

The panels 66 and 68 of the collection bag 64 and panels 82 and 84 of the enclosure 80 are shown similar in size and shape. These panels are similar in area and have a height substantially greater than the width, the height being more than twice the width. All of the panels are preferably substantially transparent, that is, transparent or transluscent so blood can be seen from the exterior of the device 12.

While various methods of making the assembly 16 are possible, one preferred method includes forming each side of the bag assembly 16 including a bag panel, a stiffener panel, and an enclosure panel independently and then welding two such sides together with the manifold 69, filter 102, and outlet 73 between the sides by weld 70 to complete the bag assembly. Each side may be independently made for example, by placing a precut stiffener between two oversize sheets of pliable plastic and heat seaming or welding in a manner to form an initial seam defining the periphery of these panels to provide one side. The initial seams of two such side assemblies may be placed substantially in registration and the two assemblies welded together by weld 70. Weld 70 may weld these initial welds together or extend adjacent to them. The plastic sheet material outwardly of the weld 70 is removed as waste to provide a completed bag or finished assembly 16. The collection bag panel and the enclosure panel of each side are in close contact with substantially the entire surfaces of the opposite sides or faces of the stiffener panel.

By making each half or side of the assembly 16 independently of the other half, additional seams such as welded seams can be readily formed between each bag panel and the enclosure panel within the slots of the stiffener panel in each side of the bag assembly, for example, welds such as indicated at 106, 107, 108, and 109 in FIG. 3, and at 112 and 114 in FIG. 4. These additional welds seams are shown adjacent the edges of the stiffener member slots to positively fix or locate each stiffener panel relative to its associated bag and enclosure panel. These additional welds along with the peripheral welds such as weld seam 70 prevent any shifting of the stiffeners relative to panels of the bag assembly 16. By fixing each stiffener panel in place in each side assembly and then welding the side assemblies together, the longer edges of the two stiffener members cannot slip over or past each other when the assembly is expanded in the holder 18, thereby making assembly 16 more rigid and resistant to collapse when the interior of the collection bag 64 is inserted into the holder 18 and subjected to suction during operation of the chest drainage system.

The assembly 16 may be inserted into the holder 18 to effect expansion of the assembly as in FIGS. 1, 6 and 7 and then both the holder and assembly sterilized such as by any suitable conventional method, for example, by employing ethlyene oxide (ETO). Depending upon the material of the stiffeners 76 and 78, the heat of sterilization may impart a permanent set or bias to the stiffeners so that when the assembly 16 is removed from the holder after filling with body fluid or blood, the stiffeners will tend to retain the shape they had while in the holder. It has been found that when the stiffeners are made of a suitable resilient semi-rigid PVC, the above sterilization method generally causes the stiffeners to take a set, that is, assume a bowed shape as shown in FIGS. 1, 6 and 7. However, when the assembly 16 was used to reinfuse collected blood with the inlet 22 and outlet 30 closed, the assembly collapsed as blood left the outlet 73 without the need to pressurize or apply a compressive force on the collection assembly. While the material used in making the stiffener panels should be rigid or stiff enough to maintain a bowed configuration in the holder 18 under expected operating suction forces, it is preferred that the material when the bag assembly 16 is removed from the holder 18 for reinfusion, should collapse as blood flows out of outlet 73 without the need to pressurize the interior or compress the exterior of the bag assembly 16.

With this construction, the bag assembly 16 readily takes on the desired predetermined configuration because of the predetermined dimensions of the rigid holder 18, and such shape will be maintained at the normal levels of suction used so that each bag manufactured will have substantially the same predetermined internal volume during operation of the chest drainage system and such assemblies can therefore be calibrated to provide acurate indications of the volume of blood collected at any time. Calibration marks (not shown) may be provided on the holder 18 and may be, for example, graduations in centiliters.

The holder 18 has a cylindrical inner wall 120 providing a cylindrical chamber for receiving the bag assembly 16 and maintaining the bag assembly 16 in a generally cylindrical shape. The holder 18 is sized to have the space between the opposed sidewalls or diameter of the chamber in the illustrated embodiment, less than the width of the bag assembly 16 when the assembly 16 is in its flattened condition (FIG. 3) so that the opposed chamber sidewalls will continuously exert the necessary compressive forces on sides 71 and 72 (FIG. 3) of the bag assembly 16 and opposed side edges of the stiffener members 88 and 89 to maintain the bag assembly in an expanded condition a shown in FIGS. 1, 6 and 7.

When the chest drainage system 10 is operating as shown in FIG. 1, blood and gas flow from the plueral cavity of patient 20 through the inlet 22 into the interior of filter 100. Blood filters through the filter and flows downwardly into the blood collection chamber 96 of the collection bag 64 while gas and air from the inlet 22 flows under the force of suction to the interior of the filter and then, without passing the filter, into the gas outlet 30. The gas flows from outlet 30 into tube 34 and the chamber 40 by way of inlet 38 of the chest drainage unit 14. Filter 100 catches solid or semi-solid particles within the filter allowing filtered blood to flow into the lower or main collection bag 64 below the filter. Since air or gas from the inlet 22 can pass directly to outlet 30, that is, without passing through the walls of the filter 100, the suction or negative pressure does not cause blood within the filter to mix with air and cause foaming.

The drainage system 10 provides a safeguard, in that, should the filter become blocked to the point that blood can no longer pass through the filter or the collection bag 64 becomes filled, further blood emanating from the patient will continue to flow out through the outlet tube 30 and into the collection chamber 40 of the chest drainage unit 14, thus protecting the patient by maintaining normal suctioning.

When it is desired to infuse the patient with his own blood, tube clamps indicated at 154 and 156 and a patient tube clamp 160, which are open during blood collection, are actuated to close tubes 24 and 28 and 32. Then the patient tube 28 and tube 34 may be disconnected from the tube connectors 26 and 36 so as to free the autotransfusion device 12 including assembly 16 and holder 18 from the chest drainage unit 14. Tubes 28 and 34 are then connected together and the patient tube clamp 160 released so that patient chest drainage suction is returned and blood will flow into chamber 40. Next, the blood collection and reinfusion bag assembly 16 can be slid upwardly and out of holder 18 and connected to a suitable frame or the like near the patient such as by using a hanger strap that may be provided at the top of the unit, such as indicated at 164 in FIG. 1. By momentarily releasing clamp 156 and gently squeezing the bag assembly 16, excess air can be eliminated from the bag. Next, cap 75 at the bottom of the bag assembly can be removed from the blood outlet 72 whereupon a conventional spike connector (not shown) can be inserted through the piercable plug 74 in outlet 73, the spike being connected to an infusion tube or catheter via a filter and drip chamber to infuse the patient's blood from the bag back into the same patient.

Should it be deemed necessary to collect more blood for reinfusion purposes to the patient, a new autotransfusion device including assembly 16 and a holder 18 may be connected to housing 39 of unit 14. To reconnect, the patient tube clamp 160 must be closed, the patient tube 28 disconnected from the tube 34 and reconnected to the bag assembly inlet connector 26. Tube 34 is then connected to bag asembly outlet 30. Functioning is resumed by releasing patient tube clamp 160.

The stiffener 76 and 78 are secured in place between the collection bag panels and enclosure panels so that there is no need to heat bond or cement the stiffeners to any of the panels. This allows use of a greater variety of materials that can be used in making the panels and stiffeners including those materials which are difficult to bond together. Where the stiffeners are not bonded or cemented to the collection bag 64 or enclosure 80, the chance of tears or breakage in the panels of either due to flexing of the materials during expansion and collapse of the assembly 16 is reduced. Also, the chance of blood leakage from the assembly 16 is reduced since a break in both the collection bag 64 and the enclosure 80 would have to occur and such breaks would have to be located in such a manner as to allow blood to flow from the collection bag and through the enclosure to the exterior of the assembly.

The stiffener members 76 and 78 of bag assembly 16, when the assembly is in the holder 18, provide the blood collection container bag of predetermined volume similar to a container having rigid sidewalls. At the same time, since the blood collection bag assembly 16 is also collapsible, it can be used similar to a conventional collapsible blood collection bag. Also, a conventional well-known blood bag pressurizing sleeve can be used where desired or required to squeeze the assembly 16 to thereby infuse blood at a rate faster than that accomplished by use of gravity only.

Preferably, the autotransfusion device 12 is assembled at the factory so that the bag assembly 16 is in the expanded condition in the holder 18 with sterile air in the bag 64. However, where desired, the bag assembly 16 could be supplied and stored in a flattened or collapsed condition under certain conditions.

The holder 18 and chest drainage device housing may be formed of a hard material, for example, an acrylic material or other relatively rigid plastic. Preferably, the stiffener panels, holder, bag assembly and chest drainage unit are formed of transparent plastic materials so that blood can be seen and monitored during operation of the system.

As various changes could be made in the above construction and without departing from the scope of the invention, it is intended that all matter contained in the above description and drawings shall be intepreted as illustrative and not in a limiting sense.

What is claimed is:

1. A body fluid collection device comprising a collapsible fluid collection bag assembly including a collapsible fluid collection bag having opposed flexible sidewalls in close facing relation when said bag is collapsed, an inlet adjacent one end of said assembly in fluid communication with the interior of said bag for receiving body fluid, an outlet adjacent said one end of said assembly in fluid communication with the interior of said bag for connection with a source of suction, a pair of stiffener members of stiffer material than that of said sidewalls and disposed adjacent the exterior sides of said sidewalls resptectively, and enclosure means sealingly enclosing and securing said stiffener members between said bag and said enclosure means, said stiffener members having portions between opposed side edges thereof bendable outwardly in opposite directions to expand the interior of said bag in response to predetermined compressive forces applied to the opposed side edges thereof.

2. The device of claim 1 wherein said sidewalls of said bag and said enclosure means are of pliable plastic material.

3. The device of claim 2 wherein said enclosure means includes a a pair of panels respectively sealed along the peripheries thereof to said bag sidewall to effect a sealed chamber.

4. The device of claim 3 wherein said stiffener members are discreet panels of relatively rigid flexible plastic material.

5. The device of claim 4 wherein said enclosure sidewall and said bag are discreet members.

6. The device of claim 1 wherein said bag and said enclosure means are in close contact engagement over substantially the entire surfaces of said stiffener members.

7. The device of claim 1 further including a fluid outlet communicating with the interior of said bag and connected at the opposite end of said bag for draining fluid collected in said bag therefrom.

8. The device of claim 1 wherein said enclosure means is connected to said bag in air-tight relation therewith.

9. The device of claim 1 wherein each of said stiffener members has upper and lower end portions with each end portion having a pair of slots extending inwardly from said opposed side edges, and a weld seam connecting each panel to said enclosure means within said slots thereby limiting endwise movement of said stiffener members relative to said bag and said enclosure means.

10. The device of claim 1 wherein said fluid collection bag and said enclosure means are of thermoplastic materials and connected together by peripheral weld means.

11. The device of claim 10 wherein said material of said collection bag is polyurethane.

12. The device of 11 wherein the materials of said collection bag, said enclosure means and said stiffener members are substantially transparent.

13. The device of claim 1 wherein each of said stiffener members extends substantially the length of said sidewalls to expand substantially the entire interior of said bag when expanded, and a holder for receiving said bag assembly having opposed wall portions engaging the opposed sides of the device and spaced apart a distance less than the distance between said opposed side edges of said stiffener members to maintain said bag expanded.

14. A body fluid collection device comprising a collapsible fluid collection bag assembly including a pair of flexible panels connected along peripheral portions thereof to form a collapsible fluid collection bag, an inlet in fluid communication with the interior of said bag for receiving body fluid, a pair of stiffener members of stiffer material than that of said panels adjacent the exterior sides of said panels respectively, enclosure means sealingly connected to said panels and securing said stiffener members between said bag and said enclosure means, said stiffener members having portions between opposed side edges thereof bendable outwardly in opposite directions to expand said bag in response to predetermined compressive forces applied to the opposed side edges thereof, and a holder removably receiving said bag assembly having opposed walls spaced apart a distance less than the distance between the opposed side edges of said stiffener members to apply a compressive force thereon and maintain said bag assembly expanded within said holder.

15. The device of claim 14 wherein said holder is generally cylindrical and the diameter of the interior thereof is less than the width of said collection bag assembly in a flattened condition.

16. The device of claim 14 including an outlet connection in fluid communication with the interior of said bag and connectable to a source of suction, said inlet and said outlet being connected at one end of said bag assembly, and a fluid outlet communicating with the interior of said bag and connected at the opposite end of said bag for draining fluid collected in said bag therefrom wherein said stiffener members are made of a plastic having a predetermined stiffness such that when said portions of said stiffener members are bent outwardly in said holder they resist collase when suction is applied to the interior of said collection bag and when said collection bag assembly is removed from said holder said stiffener members collapse upon drainage of fluid from said collection bag in the absense of positive pressurization of the interior of said collection bag and the absense of the application of positive compressive forces being applied to the exterior of said assembly.

17. The device of claim 16 wherein said stiffener members are of polyvinyl chloride.

18. A body fluid collection device comprising a collapsible fluid collection bag assembly including a pair of flexible panels connected along peripheral portions thereof to form a collapsible fluid collection bag, an inlet in fluid communication with the interior of said bag for receiving body fluid, a pair of stiffener members of stiffer material than that of said panels adjacent the exterior sides of said panels respectively, enclosure means sealingly connected to said panels and securing said stiffener members having portions between opposed side edges thereof bendable outwardly in opposite directions to expand said bag in response to predetermined compressive forces applied to the opposed side edges thereof, and an outlet connected in fluid communication with the interior of said bag and connectable to a source of suction, said inlet and said outlet being connected at one end of said bag assembly.

19. A method of making a collapsible blood collection autotransfusion bag assembly comprising the stepps of providing a pliable plastic bag, positioning a pair of relatively rigid stiffener members adjacent the opposed sides thereof, connecting an enclosure to said bag enclosing the stiffener members between the bag and the enclosure, connecting an inlet, a gas outlet, and a blood outlet in fluid communication with the interior of the bag.

20. A method of making a body fluid collection device comprising the steps of making two sides of the device each including stacking two sheets of a pliable plastic material and a preformed panel of relatively stiff material between the two sheets with the pliable sheets extending beyond the periphery of the relatively stiff panel, welding a seam connecting the pliable panels together beyond the periphery of the stiff panel to seal and enclose the stiff panel between the sheets, positioning fluid inlet and gas outlet passageways between the two sides adjacent one of the ends thereof and a fluid outlet between the two sides adjacent the opposite end therof, and welding the two sides of the device together with the fluid inlet and gas outlet passageways connected between the two sides of the device at the one end of the device and the fluid outlet at the opposite end of the device.

21. A method of making a body fluid collection device comprising the steps of making two sides of the device each including stacking two sheets of a pliable plastic material and preformed panel of relatively stiff material between the two sheets with the pliable sheets extending beyond the periphery of the relative stiff panel, welding a seam connecting the pliable panels together beyond the periphery of the stiff panel to seal the stiff panel between the sheets, welding the two sides of the device together with an inlet and a gas outlet connected between the sides of the device at the top thereof, the stiffener members having slots formed therein to provide end portions thereof that are bendable in planes intersecting the longitudinal axis of the members, and weld seaming the two sheets of pliable plastic material together within each of said slots in each of the sides of the device.

22. The method of claim 21 wherein said stiffener members are formed of a relatively rigid plastic sheet material, and including the steps of inserting the fluid collection device in a holder which compresses opposed side edges of the device to bend the stiffener members and expand the bag, and sterilizing the device while in the holder.

23. The method of claim 22 wherein said sheet material is polyvinyl chloride and takes a bent set during sterilization step.

* * * * *